United States Patent
Cho et al.

(10) Patent No.: US 8,268,397 B2
(45) Date of Patent: Sep. 18, 2012

(54) ORGANOMETALLIC PRECURSOR, THIN FILM HAVING THE SAME, METAL WIRING INCLUDING THE THIN FILM, METHOD OF FORMING A THIN FILM AND METHOD OF MANUFACTURING A METAL WIRING USING THE SAME

(75) Inventors: Youn-Joung Cho, Suwon-si (KR); Jung-Ho Lee, Suwon-si (KR); Jun-Hyun Cho, Suwon-si (KR); Seung-Min Ryu, Busan (KR); Kyoo-Chul Cho, Yongin-si (KR); Jung-Sik Choi, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 780 days.

(21) Appl. No.: 12/219,983

(22) Filed: Jul. 31, 2008

(65) Prior Publication Data
US 2009/0035516 A1   Feb. 5, 2009

(30) Foreign Application Priority Data
Aug. 3, 2007   (KR) .................. 10-2007-0078188

(51) Int. Cl.
*B05D 1/36* (2006.01)
*C23C 16/00* (2006.01)

(52) U.S. Cl. ................. 427/250; 427/255.26; 427/124; 427/123

(58) Field of Classification Search ............... 427/248.1, 427/255.28
See application file for complete search history.

(56) References Cited

U.S. PATENT DOCUMENTS
2007/0066061 A1 *   3/2007   Choi et al. ................ 438/688

FOREIGN PATENT DOCUMENTS
| JP | 09-012581 | 1/1997 |
| KR | 100233961 | 9/1999 |
| KR | 1020000022650 | 4/2000 |
| WO | WO 2007136184 A1 * | 11/2007 |

OTHER PUBLICATIONS

Glass et al. Chemical Vapor Deposition Precursor Chemistry. 2. Formation of Pure Aluminum, Alumina, and Aluminum Boride Thin Film from Boron Containing Precursor Compounds by Chemical Vapor Deposition. Chem. Mater. 1992, 4, 530-538.*

* cited by examiner

*Primary Examiner* — David Turocy
(74) *Attorney, Agent, or Firm* — Harness, Dickey & Pierce, P.L.C.

(57) ABSTRACT

Disclosed are an organometallic precursor that may be used in manufacturing a semiconductor device, a thin film having the same, a metal wiring including the thin film, a method of forming a thin film and a method of manufacturing a metal wiring. An organometallic precursor including a central metal, a borohydride ligand and an amine ligand for reducing a polarity of the organometallic precursor may be provided onto a substrate, and may be thermally decomposed to form a thin film on the substrate. The organometallic precursor having a reduced polarity may be provided to a chamber with a constant flow rate, and thus stability and/or efficiency of a semiconductor manufacturing process may be improved.

8 Claims, 11 Drawing Sheets

ORGANOMETALLIC PRECURSOR, THIN FILM HAVING THE SAME, METAL WIRING INCLUDING THE THIN FILM, METHOD OF FORMING A THIN FILM AND METHOD OF MANUFACTURING A METAL WIRING USING THE SAME

BACKGROUND

1. Field

Example embodiments relate to an organometallic precursor, a thin film having the same, a metal wiring including the thin film, a method of forming a thin film and a method of manufacturing a metal wiring using the same. More particularly, example embodiments relate to an organometallic precursor that may be used in forming a thin film of a semiconductor device, a thin film having the same, a metal wiring including the thin film, a method of forming a thin film and a method of manufacturing a metal wiring using the same.

2. Description of the Related Art

Semiconductor devices having a higher integration degree and rapid response speed are desirable. The technology of manufacturing semiconductor devices has improved the integration degree, reliability and/or response speed of semiconductor devices. As the integration degree of the semiconductor devices increases, a design rule of the semiconductor devices may decrease.

The semiconductor devices generally may include conductive structures (e.g., wirings, plugs, conductive regions or electrodes) and insulation structures (e.g., dielectric layers, or insulating interlayers) that may electrically isolate the conductive structures. Forming such structures may include a film deposition process. Examples of the film deposition process may include a physical vapor deposition (PVD) process, a chemical vapor deposition (CVD) process, or an atomic layer deposition (ALD) process.

The PVD process has an undesirable property that fills a hole, a gap or a trench, and thus generates a void in the hole, the gap or the trench. As the integration degree of the semiconductor device increases, a width of the hole may become narrow and an aspect ratio of the hole may be increased. When the width of the hole is smaller and the aspect ratio of the hole is larger, a depositing material may be readily accumulated on an entrance of the hole to block the entrance of the hole prior to completely filling the inside of the hole and to generate a void in the hole. The void may increase an electrical resistance of a conductive structure to deteriorate performance of the semiconductor device and to cause a defect of the semiconductor device. However, the CVD process or the ALD process may have an improved property that fills the hole as compared with the PVD process, and thus may be employed in filling the hole, the gap or the trench in a semiconductor manufacturing process.

SUMMARY

Example embodiments provide an organometallic precursor that may constantly maintain an inflow rate of a precursor into the chamber in a deposition process. Example embodiments also provide a thin film and a method of forming a thin film including the organometallic precursor. Example embodiments also provide a metal wiring and a method of manufacturing a metal wiring including the thin film. According to example embodiments, there may be provided an organometallic precursor that may be used for forming a thin film of a semiconductor device. The organometallic precursor may include a central metal, a borohydride ligand coordinating to the central metal, and an amine ligand coordinating to the central metal and reducing a polarity of the organometallic precursor.

In example embodiments, the amine ligand may include an amine ligand having at least one substituent selected from $C_2$-$C_{10}$ alkyl, cycloalkyl and aryl, or a nonaromatic heterocyclic amine ligand. In example embodiments, the organometallic precursor may include a compound having a chemical structure represented by Formulas 1 through 3,

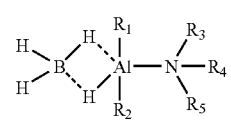

[Formula 1]

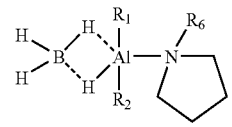

[Formula 2]

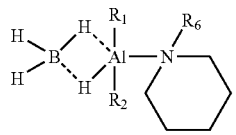

[Formula 3]

wherein $R_1$ and $R_2$ may be each independently hydrogen or $C_1$-$C_4$ alkyl, $R_3$, $R_4$ and $R_5$ may be each independently hydrogen, $C_1$-$C_{10}$ alkyl, cycloalkyl or aryl, provided that compounds wherein all of $R_3$, $R_4$ and $R_5$ are hydrogen, methyl, or a combination of hydrogen and methyl may be excluded, and $R_6$ may be hydrogen or $C_1$-$C_4$ alkyl.

In example embodiments, the organometallic precursor may include a compound having a chemical structure represented by Formula 4.

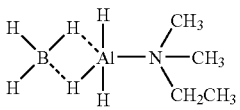

[Formula 4]

In example embodiments, the central metal may include at least one selected from aluminum, titanium, zirconium, vanadium, niobium, tantalum, hafnium, lanthanum, tungsten and copper. In example embodiments, the organometallic precursor may have an electrical conductivity substantially lower than or equal to about 10 μS/cm. In example embodiments, the organometallic precursor may have an electrical conductivity substantially lower than or equal to about 6 μS/cm.

According to example embodiments, there is provided a thin film and a metal wiring. The thin film may include the organometallic precursor of example embodiments on a substrate. The metal wiring may include an insulation layer pattern having an opening on a substrate, the opening exposing a conductive structure of the substrate, and a first metal film on the insulation layer pattern and a bottom and sidewalls of the opening, wherein the first metal film is the thin film of example embodiments.

According to example embodiments, there may be provided a method of forming a thin film on a substrate. In the method, an organometallic precursor including a central metal, a borohydride ligand, and an amine ligand for reducing a polarity of the organometallic precursor may be provided onto the substrate, and the organometallic precursor may be decomposed to form the thin film on the substrate. In example embodiments, the organometallic precursor may be vaporized using a carrier gas in a bubbling system prior to providing the organometallic precursor onto the substrate. In example embodiments, the organometallic precursor may be vaporized at a temperature of about 20° C. to about 50° C. prior to providing the organometallic precursor onto the substrate. In example embodiments, the organometallic precursor may be thermally decomposed at a temperature of about 100° C. to about 300° C.

According to example embodiments, there may be provided a method of manufacturing a metal wiring. In the method, an insulation layer may be formed on a substrate having a conductive structure, and the insulation layer may be partially removed to form an insulation layer pattern having an opening that exposes the conductive structure. A first metal film may be formed on the insulation layer pattern and a bottom and sidewalls of the opening, and the first metal film may be formed by using the method of forming a thin film according to example embodiments.

According to example embodiments, the organometallic precursor including the amine ligand may have a reduced polarity, and thus, interaction between molecules of the organometallic precursor may also be reduced. Due to the reduced molecular interaction, a vaporizing rate of the organometallic precursor may be improved. Further, the vaporizing rate of the organometallic precursor may not be substantially reduced, for example, in a bubbling system while process time passes and/or the amount of the precursor contained in a canister varies. Accordingly, when films are formed on a large number of wafers using the organometallic precursor, an inflow rate of the precursor and a deposition rate of the film may not be substantially reduced and may be constantly maintained. Thus, films with relatively uniform thickness and electrical and/or physical characteristics may be steadily manufactured.

Furthermore, according to example embodiments, the organometallic precursor may have improved thermal and/or chemical stabilities owing to the borohydride ligand. When films are formed using the organometallic precursor, generation of impurities including carbon may be reduced or suppressed to decrease an electrical resistance of the film, and a thermal stress on an underlying structure may be reduced. Therefore, stability, efficiency and/or reliability of a semiconductor manufacturing process may be enhanced.

BRIEF DESCRIPTION OF THE DRAWINGS

Example embodiments will be more clearly understood from the following detailed description taken in conjunction with the accompanying drawings.

FIG. 1 is a flow chart illustrating a method of forming a thin film in accordance with example embodiments;

FIGS. 2 through 6 are cross-sectional views illustrating a method of manufacturing a metal wiring in accordance with example embodiments;

FIGS. 7 and 8 are graphs illustrating $^1$H NMR spectrums of the organometallic precursors prepared in Example 1 and Comparative Example 1;

FIGS. 9 and 10 are graphs illustrating variations in a peak height of $^1$H NMR spectrum and a UV-VIS transmittance with the passage of time while the organometallic precursors prepared in Example 1 and Comparative Example 1 were maintained at about 100° C.;

FIGS. 11 and 12 are graphs illustrating variations in a peak height of $^1$H NMR spectrum and a UV-VIS transmittance with the passage of time while the organometallic precursors prepared in Example 1 and Comparative Example 1 were maintained at about 20° C.;

FIG. 13 is a graph illustrating temperature dependency of a vapor pressure of the organometallic precursor prepared in Example 1;

FIGS. 14 and 15 are graphs illustrating results of a thermal gravimetric analysis (TGA) and a differential thermal analysis (DTA) with regard to the organometallic precursors prepared in Example 1 and Comparative Example 1;

FIG. 16 is a graph illustrating variation of sheet resistances of aluminum films formed on wafers in accordance with an increase of the number of the wafers while the aluminum films were formed using the organometallic precursor of Example 1; and FIG. 17 is a graph illustrating variation of deposition time in accordance with an increase of the number of the wafers while films were formed on the wafers to have a predetermined or given thickness using the organometallic precursor of Example 1 and Comparative Example 1.

Figure 1:
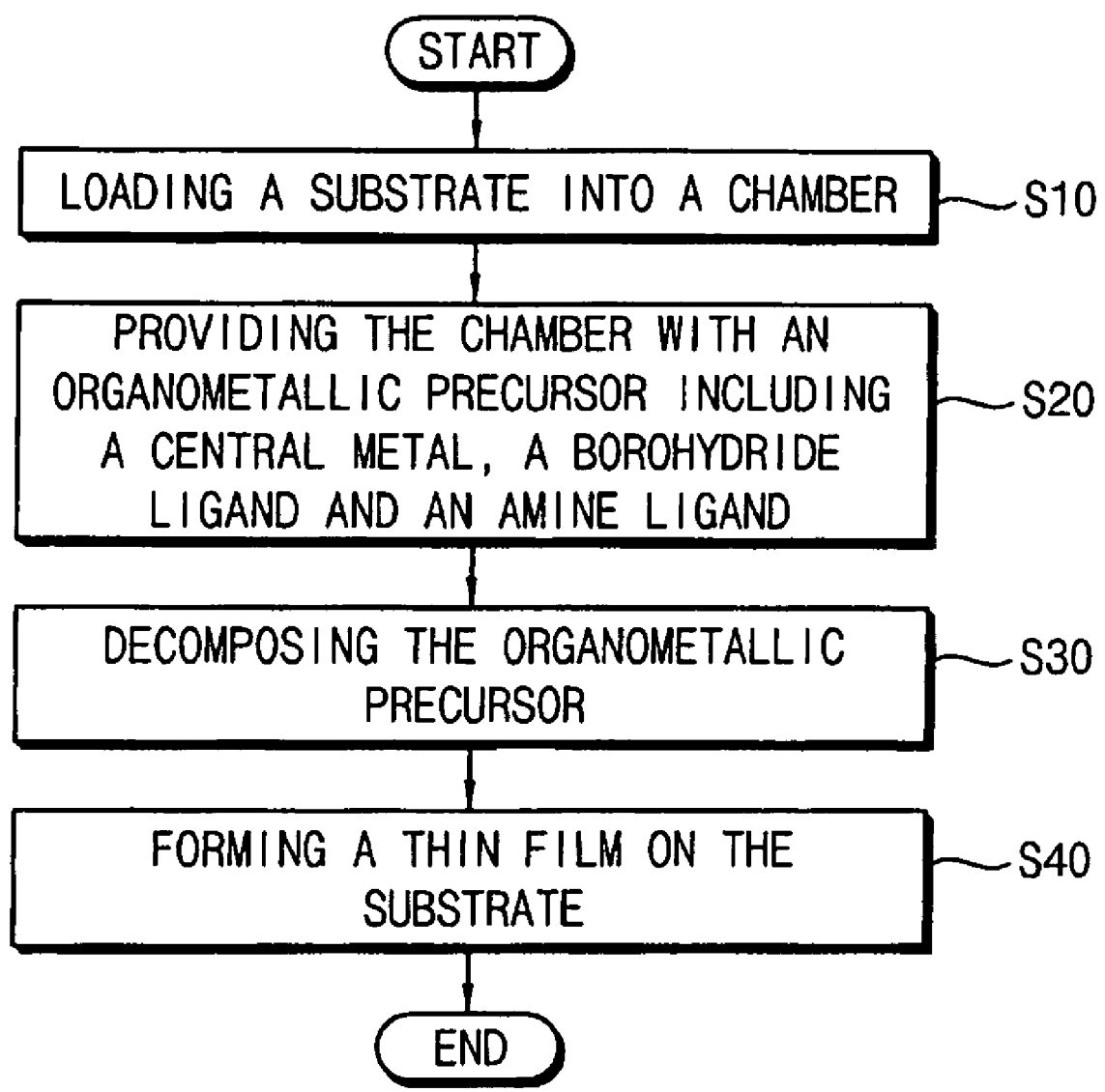
FIGS. 1-17 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

This application claims priority under 35 U.S.C. §119 to Korean Patent Application No. 2007-78188, filed on Aug. 3, 2007, in the Korean Intellectual Property Office (KIPO), the entire contents of which are herein incorporated by reference.

Various example embodiments will be described more fully hereinafter with reference to the accompanying drawings, in which some example embodiments are shown. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art. In the drawings, the sizes and relative sizes of layers and regions may be exaggerated for clarity.

It will be understood that when an element or layer is referred to as being "on," "connected to" or "coupled to" another element or layer, it may be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, e.g., "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would be oriented "above" the other elements or features. Thus, the exemplary term "below" may encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle may, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms including technical and scientific terms used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

According to example embodiments, an organometallic precursor may include a central metal, a borohydride ligand coordinating to the central metal, and an amine ligand coordinating to the central metal and reducing a polarity. The amine ligand may reduce polarity of the organometallic precursor and may also reduce interaction between molecules of the organometallic precursor. As a result, a vaporizing rate of the organometallic precursor may increase, and the vaporizing rate may not substantially vary while the process time passes or the amount of the organometallic precursor in a canister becomes smaller.

For example, when a precursor is vaporized in a bubbling system by bubbling the precursor in a canister with a carrier gas, there may be a tendency that the vaporizing rate decreases with the passage of the process time, because the amount of the precursor contained in the canister may decrease with the passage of the process time and the reduced amount may cause an increase in molecular interaction of the precursor. When the polarity of the precursor is large, the vaporizing rate may greatly decrease as the amount of the precursor in the canister becomes smaller. When the precursor has a relatively small polarity, molecular interaction of the precursor may be reduced, and thus, a decrease of the vaporizing rate caused by a relatively small amount of precursor may be prevented or suppressed.

The organometallic precursor may also include the borohydride ligand that bidentately coordinates to the central metal. The borohydride ligand may improve stability of the organometallic precursor, and thus, the organometallic precursor may have a stable vapor phase. Further, the organometallic precursor may have a relatively low decomposition temperature, and thus, a film may be formed using the organometallic precursor while thermal stress on an underlying structure of the film is reduced.

In example embodiments, examples of the amine ligand for reducing polarity may include an amine ligand having $C_2$-$C_{10}$ alkyl, cycloalkyl or aryl as a substituent, or a nonaromatic heterocyclic amine ligand. Examples of a $C_2$-$C_{10}$ alkyl that may be used as the substituent of the amine ligand may include ethyl, propyl, butyl, pentyl, hexyl, heptyl, octyl, nonyl, and decyl. Examples of cycloalkyl that may be used as the substituent of the amine ligand may include cyclopentyl, and cyclohexyl.

Examples of the amine ligand may include N,N-dimethylethylamine, ethylamine, propylamine, N,N-dimethylpropylamine, butylamine, N,N-dimethylbutylamine, diethylamine, N,N-diethylmethylamine, triethylamine, cyclohexylamine, N-methylcyclohexylamine, N, N-dimethylcyclohexylamine, aniline, N-methylaniline, N,N-dimethylaniline, pyrrolidine, N-methylpyrrolidine, piperidine, and N-methylpiperidine.

In example embodiments, the organometallic precursor may have a lower electrical conductivity as a criterion of a lower polarity. In example embodiments, the organometallic precursor may have an electrical conductivity lower than or equal to about 10 µS/cm. In example embodiments, the organometallic precursor may have an electrical conductivity lower than or equal to about 7 µS/cm. In example embodiments, the organometallic precursor may have an electrical conductivity substantially lower than or equal to about 6 µS/cm. In example embodiments, the organometallic precursor may include, as the central metal, metal elements in Group 13 (IIIA) (e.g., aluminum, gallium, indium or thallium) or transition metals. Examples of the central metal may include aluminum, titanium, zirconium, vanadium, niobium, tantalum, hafnium, lanthanum, tungsten, and copper.

In example embodiments, the organometallic precursor may include aluminum as the central metal. Examples of the organometallic precursor may include compounds represented by Formulas 1 through 3.

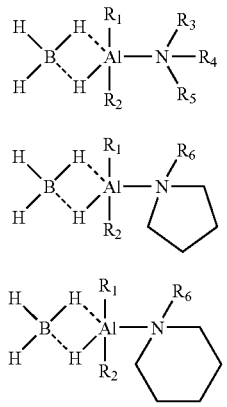

[Formula 1]

[Formula 2]

[Formula 3]

In Formulas 1 through 3, $R_1$ and $R_2$ may be each independently hydrogen or $C_1$-$C_4$ alkyl, $R_3$, $R_4$ and $R_5$ may be each independently hydrogen, $C_1$-$C_{10}$ alkyl, cycloalkyl or aryl, provided that compounds wherein all of $R_3$, $R_4$ and $R_5$ are hydrogen, methyl, or a combination of hydrogen and methyl may be excluded, and $R_6$ may be hydrogen or $C_1$-$C_4$ alkyl. Examples of hydrogen may include hydrogen ($^1$H), deuterium ($^2$H) and tritium ($^3$H). Examples of $C_1$-$C_4$ alkyl may include methyl, ethyl, propyl or butyl.

In Formula 1, $R_3$, $R_4$ and $R_5$ are a substituent of the amine ligand. $R_3$, $R_4$ and $R_5$ may be each independently $C_1$-$C_{10}$ alkyl, cycloalkyl or aryl, and at least one of $R_3$, $R_4$ and $R_5$ may be $C_2$-$C_{10}$ alkyl (e.g., ethyl, propyl, butyl, hexyl or octyl), cycloalkyl or aryl to reduce polarity of the organometallic precursor.

In example embodiments, the organometallic precursor may be a compound having a chemical structure represented by Formula 4.

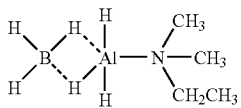

[Formula 4]

The organometallic precursor in accordance with example embodiments may have a relatively high vapor pressure at a relatively low temperature (e.g., room temperature). For example, the organometallic precursor may have a vapor pressure in a range of about 0.3 to about 0.8 Torr at a temperature of about 30° C., and a vapor pressure in a range of about 0.8 to about 3 Torr at a temperature of about 50° C. Accordingly, the organometallic precursor may be vaporized at a temperature of about 20° C. to about 50° C., and may be provided into a chamber.

In example embodiments, the organometallic precursor may be decomposed at a temperature of about 100° C. to about 300° C. In example embodiments, the organometallic precursor may be decomposed at a temperature of about 100° C. to about 200° C. The organometallic precursor may have a relatively low temperature of decomposition to reduce a deposition temperature of a film formation process. Thus, thermal stress on structures, which may be formed on or adjacent to the formed film, may be reduced or suppressed.

According to example embodiments, the organometallic precursor including the amine ligand may have a reduced polarity, and thus, interaction between molecules of the organometallic precursor may also be reduced. Due to the reduced molecular interaction, a vaporizing rate of the organometallic precursor may be improved. Additionally, although the process time passes and the amount of precursor varies, the vaporizing rate may not be substantially reduced and a deposition rate of a film may be constantly or steadily maintained.

According to example embodiments, there may be a thin film and a metal wiring. The thin film may include the organometallic precursor of example embodiments on a substrate. The metal wiring may include an insulation layer pattern having an opening on a substrate, the opening exposing a conductive structure of the substrate, and a first metal film on the insulation layer pattern and a bottom and sidewalls of the opening, wherein the first metal film is the thin film of example embodiments.

A method of forming a film using the above-mentioned organometallic precursor according to example embodiments will be described in more detail, hereinafter. FIG. 1 is a flow chart illustrating a method of forming a thin film in accordance with example embodiments. Referring to FIG. 1, a substrate, on which a film may be formed, may be positioned in a chamber in S10. Various structures (e.g., electrodes, conductive layers, insulation layers, mask layers, plugs, pads and/or conductive regions.) may be formed on the substrate. The substrate may be loaded on a susceptor located in the chamber. A temperature and/or a pressure of the chamber may be adjusted to perform a deposition process of a film.

An organometallic precursor may be introduced into the chamber in S20. The organometallic precursor may be the above-mentioned precursors according to example embodiments. For example, the organometallic precursor may include a central metal, a borohydride ligand, and an amine ligand for reducing polarity. The organometallic precursor may be provided to the chamber using a precursor providing apparatus (e.g., a bubbling system, an injection system or a liquid delivery system (LDS)). For example, when the organometallic precursor is introduced using the bubbling system, the organometallic precursor having a liquid phase may be bubbled using a carrier gas to be vaporized. The vaporized organometallic precursor may be introduced with a carrier gas into the chamber.

An inflow rate of the organometallic precursor may depend on a vaporizing rate of the organometallic precursor and/or a flow rate of the carrier gas. The vaporizing rate and/or a bubbling efficiency may be affected by polarity and/or molecular interaction of the organometallic precursor as well as an area, a period and/or a frequency of contacting between the carrier gas and the liquid organometallic precursor, and a vaporization temperature. When the organometallic precursor exhibits relatively high polarity and/or strong molecular attraction, the organometallic precursor may not be readily vaporized by bubbling and the vaporizing rate may be slower.

However, the organometallic precursor according to example embodiments may include the amine ligand capable of reducing polarity, and molecular interaction of the organometallic precursor may be relatively small or negligible. Owing to the reduced molecular attraction, the organometallic precursor may be more easily vaporized by bubbling, and the vaporizing rate may be improved. Additionally, even though the amount of the organometallic precursor may decrease, the vaporizing rate may not be reduced and may be constantly maintained, as compared with a precursor having a relatively strong molecular interaction. The organometallic precursor according to example embodiments has been previously described, so any further explanations in this regard will be omitted herein for brevity.

In example embodiments, the carrier gas being introduced with the organometallic precursor may be an inactive gas or an inert gas. Examples of the carrier gas may include an argon gas, a helium gas, a nitrogen gas, or a neon gas. These may be used alone or in a mixture thereof. In other example embodiments, a hydrogen gas may be additionally provided with the carrier gas.

A flow rate of the carrier gas may be adjusted by considering several factors including a deposition rate, a vapor pressure of the organometallic precursor, and/or a temperature. For example, the carrier gas may be provided to the chamber at a flow rate of about 200 to about 1,300 sccm (standard cubic centimeters per minute).

A canister in which the organometallic precursor may be vaporized by bubbling, a gas line which may connect the canister to the chamber, and a shower head which may spray the organometallic precursor into the chamber, may have temperatures sufficient for sustaining the vapor phase of the organometallic precursor. The organometallic precursor may have a relatively high vapor pressure at a relatively low temperature. Accordingly, temperatures of the canister, the gas line and a shower head may be low relatively. For example, temperatures of the canister, the gas line and a shower head may be in a range of about 20° C. to about 50° C., and vaporization of the organometallic precursor may be performed at such temperature range. The organometallic precursor which has been provided onto the substrate may be decomposed by heat or a chemical reaction in S30.

In example embodiments, the organometallic precursor may be thermally decomposed by a CVD process. While the organometallic precursor is decomposed, ligands may be detached from the organometallic precursor and may be discharged from the chamber together with the carrier gas. The central metal may be deposited on the substrate to form a film in S40. In example embodiments, the substrate and/or an inside of the chamber may have a temperature of about 100° C. to about 300° C. In example embodiments, the substrate and/or an inside of the chamber may have a temperature lower than about 200° C.

In example embodiments, the organometallic precursor may be chemically decomposed. For example, a metal oxide film may be formed on the substrate using the organometallic precursor and a reactive gas by a CVD process or an ALD process. In the ALD process, the organometallic precursor may be provided to the chamber with a carrier gas, and the chamber may be purged. A reactive gas, e.g., an oxygen gas, an ozone gas or water vapor, may be provided to the chamber to generate an oxidation reaction between the organometallic precursor and the reactive gas, and the chamber may be purged again. These steps may be performed at least once to form a film of metal oxide on the substrate in S40.

In methods of forming a film according to example embodiments, the film may be formed using the organometallic precursor including the amine ligand. The organometallic precursor may have a reduced polarity, and thus, interaction between molecules of the organometallic precursor may also be reduced. Due to the reduced molecular interaction, a vaporizing rate of the organometallic precursor may be improved. Additionally, although the process time passes and the amount of precursor varies or decreases, the vaporizing rate may not be reduced and a deposition rate of a film may be constantly maintained. Thus, the film of which thickness and electrical and/or physical characteristics may be substantially uniform may be steadily manufactured.

Figure 2:
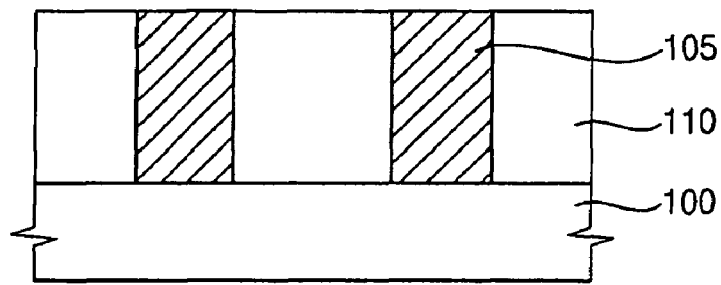

A method of manufacturing a metal wiring using the above-mentioned organometallic precursor according to example embodiments will be described in more detail, hereinafter. FIGS. 2 through 6 are cross-sectional views illustrating a method of manufacturing a metal wiring in accordance with example embodiments. FIG. 2 is a cross-sectional view illustrating a conductive structure and a first insulation layer pattern formed on a substrate.

Referring to FIG. 2, a substrate 100 on which a conductive structure 105 is formed may be prepared. Non-limiting examples of the conductive structure 105 may include a contact region doped with impurities, a gate electrode, a capacitor electrode, a contact, a pad, and a plug. A first insulation layer (not shown) may be formed on the substrate 100 to cover the conductive structure 105, and an upper portion of the first insulation layer may be removed until a top surface of the conductive structure 105 may be exposed. As a result, a first insulation layer pattern 110 may be formed on the substrate 100. The first insulation layer pattern 110 may be formed using an insulation material (e.g., oxide, nitride, and/or oxynitride). For example, the first insulation layer pattern 110 may be formed using silicon oxide (e.g., phosphosilicate glass (PSG), borophosphosilicate glass (BPSG), undoped silicate glass (USG), spin-on glass (SOG), tetraethyl orthosilicate (TEOS), plasma-enhanced TEOS (PE-TEOS), or high density plasma chemical vapor deposition (HDP-CVD) oxide).

Figure 3:
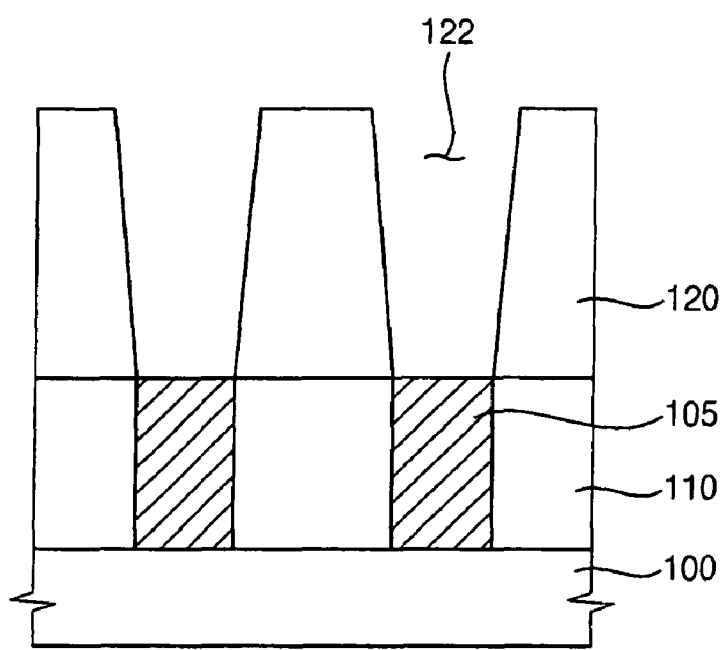

FIG. 3 is a cross-sectional view illustrating a second insulation layer pattern having an opening that exposes the conductive structure. Referring to FIG. 3, a second insulation layer (not shown) may be formed on the conductive structure 105 and the first insulation layer pattern 110. The second insulation layer may be formed using an insulation material (e.g., oxide, nitride, and oxynitride). In example embodiments, the second insulation layer may be formed using the same material as that of the first insulation layer pattern 110. In example embodiments, the second insulation layer may be formed using a material different from that of the first insulation layer pattern 110.

In example embodiments, prior to forming the second insulation layer, an etch stop layer (not illustrated) may be formed on the conductive structure 105 and the first insulation layer pattern 110. The etch stop layer may prevent or reduce the conductive structure 105 and the first insulation layer pattern 110 from being damaged while an opening 122 may be formed on the second insulation layer in a subsequent process. The etch stop layer may be formed using a material having an etching rate substantially lower than an etching rate of the second insulation layer. For example, when the second insulation layer is formed using oxide, the etch stop layer may be formed using nitride or metal oxide. After forming the opening 122 in the second insulation layer, an exposed portion of the etch stop layer on the conductive structure 105 may be removed by a wet etching process.

The second insulation layer may be partially removed to form a second insulation layer pattern 120 having the opening 122 that may expose a top surface of the conductive structure 105. In example embodiments, a photoresist film (not illustrated) may be formed on the second insulation layer. An exposure process and a developing process may be carried out on the photoresist film to form a photoresist pattern (not illustrated) on the second insulation layer. The second insulation layer may be partially etched using the photoresist pattern as an etching mask to form the opening 122 in the second insulation layer. In example embodiments, the opening 122 may have a round shape or a line shape extending along a predetermined or given direction.

Figure 4:
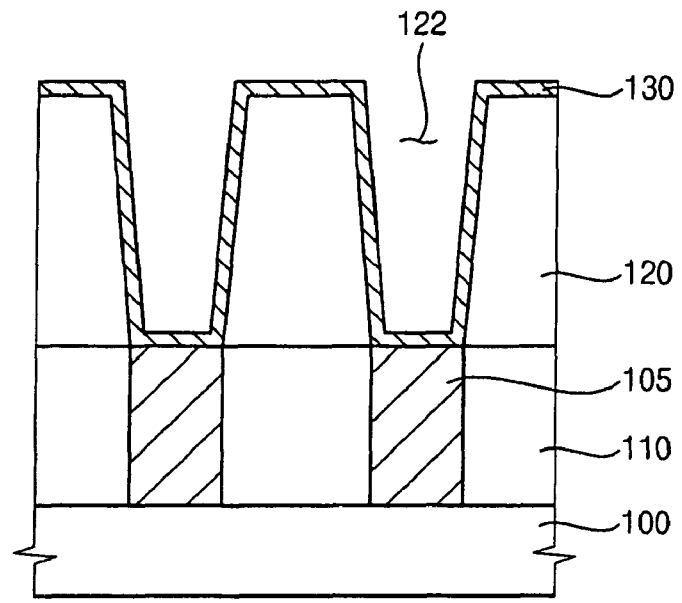

FIG. 4 is a cross-sectional view illustrating a barrier layer formed on a bottom and sidewalls of the opening and on a top surface of the second insulation layer pattern. Referring to FIG. 4, a barrier layer 130 may be formed on sidewalls and a bottom of the opening 122 and on a top surface of the second insulation layer pattern 120. The barrier layer 130 may be formed to have a substantially uniform thickness. The barrier layer 130 may inhibit a metal of a first metal layer 140 (see FIG. 5) and a second metal layer 150 (see FIG. 6) from being diffused into the second insulation layer pattern 120 and the first insulation layer pattern 110.

The barrier layer 130 may have improved adhesiveness, lower contact resistance, higher resistance against thermal or mechanical stress and/or higher conductivity. In example embodiments, the barrier layer 130 may be formed using titanium, titanium nitride, tantalum, or tantalum nitride. The barrier layer 130 may be formed using a CVD process, a sputtering process and/or an ALD process.

Figure 5:
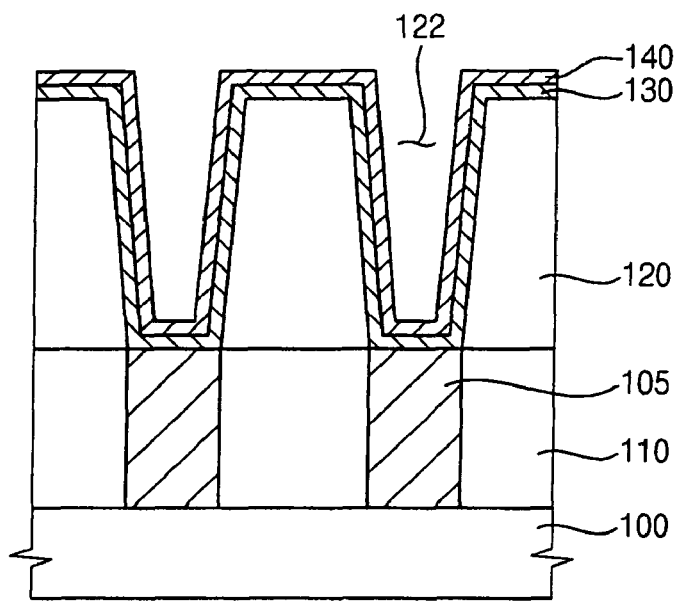

FIG. 5 is a cross-sectional view illustrating a first metal layer formed on the barrier layer. Referring to FIG. 5, a first metal layer 140 may be formed on the barrier layer 130. In example embodiments, the first metal layer 140 may be formed using the above-mentioned organometallic precursor according to example embodiments. The first metal layer 140 may be formed to have a predetermined or given thickness, and may be formed on a bottom and sidewalls of the opening 122 and on the barrier layer 130 positioned on the top surface of the second insulation layer pattern 120. For example, the first metal layer 140 may be formed by a CVD process having improved step coverage. The CVD process may be carried out using the organometallic precursor according to example embodiments. In example embodiments, the organometallic precursor may have at least one of aluminum, tungsten and copper as a central metal. In example embodiments, the organometallic precursor may include aluminum as the central metal. When the organometallic precursor includes aluminum, the first metal layer 140 may be an aluminum layer.

In example embodiments, the organometallic precursor may be introduced with a carrier gas onto the substrate 100 on which the barrier layer 130 may be formed. The organometallic precursor may include an amine ligand for reducing polarity. A vaporizing rate of the organometallic precursor may not be reduced, although the amount of the organometallic precursor decreases with the passage of process time. Thus, the organometallic precursor may be provided onto the substrate 100 with a constant flow rate. For example, the organometallic precursor may be thermally decomposed at a temperature of about 100° C. to about 300° C. Ligands separated from the organometallic precursor may be removed with the carrier gas, and the central metal may be deposited on the barrier layer 130 to form the first metal layer 140. The organometallic precursor has been previously described, so any further explanations in this regard will be omitted herein.

The first metal layer 140 may be provided as a seed layer while the second metal layer 150 (see FIG. 6) may be subsequently formed on the first metal layer 140 to fill the opening 122. The first metal layer 140 may also increase flowability of a material that forms the second metal layer 150, and thus the material of the second metal layer 150 may readily move into the opening 122. Further, the first metal layer 140 may improve adhesiveness of the second metal layer 150 to the barrier layer 130.

Figure 6:
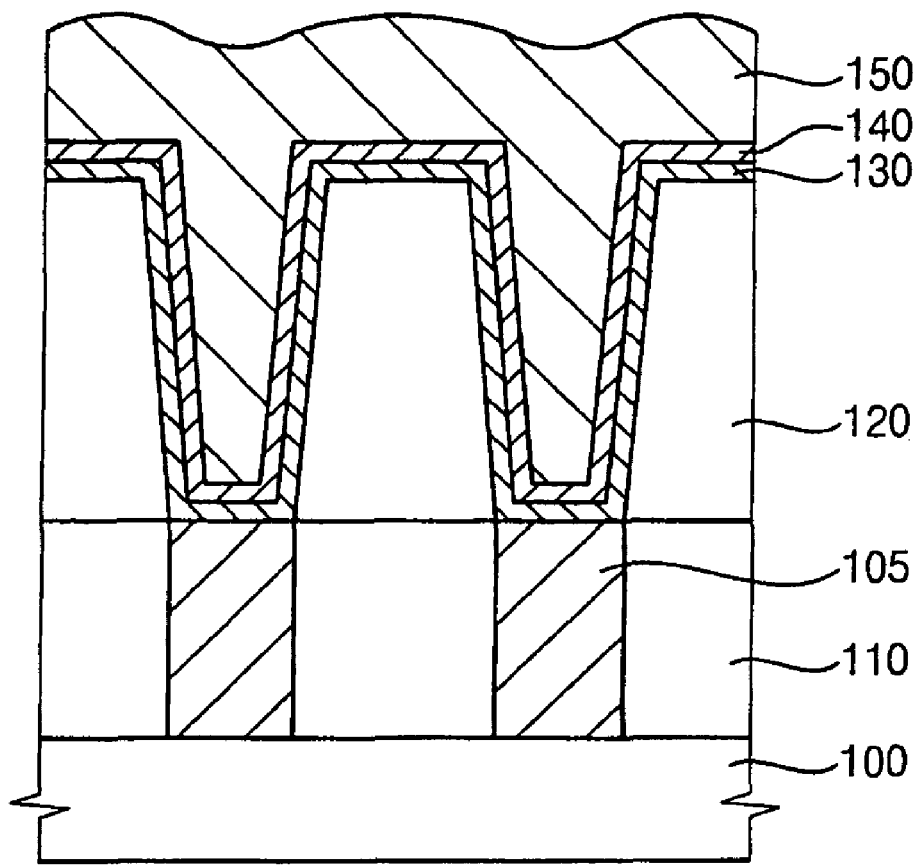

FIG. 6 is a cross-sectional view illustrating a second metal layer formed on the first metal layer. Referring to FIG. 6, the second metal layer 150 may be formed on the first metal layer 140 to fill the opening 122. The second metal layer 150 may be formed using a material substantially the same as that of the first metal layer 140. In example embodiments, the second metal layer 150 may be formed using a material substantially different from that of the first metal layer 140. The second metal layer 150 may be formed by a CVD process and/or a PVD process. In example embodiments, the second metal layer 150 may be formed by performing a PVD process (e.g., a direct current sputtering, an alternating current sputtering and/or a direct current magnetron sputtering).

In example embodiments, a metallic material may be deposited on the first metal layer 140 by the PVD process, and may be reflowed by thermally treating the substrate 100 at a temperature of about 350° C. to about 550° C. for from about several seconds to about several hundred seconds. The reflow process may be carried out under a high vacuum condition to reduce oxidation of the metallic material. By performing the reflow process, the second metal layer 150 may be formed to have a flat surface and to fill the opening 122 without forming a void in the opening 122. As a result, a metal wiring, which may include the first metal layer 140 and the second metal layer 150 and may be electrically connected to the conductive structure 105, may be formed on the substrate 100.

In methods of forming a metal wiring according to example embodiments, the metal wiring may be formed using the organometallic precursor including the amine ligand. The organometallic precursor may have a reduced polarity, and thus, interaction between molecules of the organometallic precursor may also be reduced. Due to the reduced molecular interaction, a vaporizing rate of the organometallic precursor may be improved. Additionally, although the process time passes and the amount of precursor varies, the vaporizing rate may not be substantially reduced and a deposition rate of a film may be constantly maintained. Accordingly, when metal wirings are formed on a relatively large number of wafers using the organometallic precursor, an inflow rate of the precursor and a deposition rate may not be substantially reduced and/or may be constantly maintained. Thus, metal wirings, of which thickness and electrical and/or physical characteristics are substantially uniform, may be steadily manufactured.

Example embodiments will be described in more detail with reference to Example, Comparative Example and Evaluations for organometallic precursors, hereinafter.

Preparation Of Organometallic Precursor

EXAMPLE 1

About 453.32 g of aluminum chloride ($AlCl_3$) was diluted with about 2 L of ethyl ether and about 180.63 g of lithium aluminum hydride ($LiAlH_4$) was diluted with about 1.5 L of ethyl ether. Reactants were cooled to a temperature of about −30° C. The solution including aluminum chloride was added to the solution including lithium aluminum hydride, and was mixed together. About 401.91 g of N,N-dimethylethylamine ($NEtMe_2$) was added to the solution including aluminum chloride and lithium aluminum hydride. The reaction was carried out for about five hours. The solution including a reaction product, $ClAlH_2NEtMe_2$, was filtered. About 514.44 g of sodium borohydride ($NaBH_4$) was diluted with about 2 L of ethyl ether. The solution including $ClAlH_2NEtMe_2$ was dropped into the sodium borohydride solution for about 30 minutes. The mixture was reacted for about 20 hours, and filtered to remove solvent from the mixture. The filtered resultant was purified by a vacuum evaporation. As a result, a colorless and liquid product was obtained.

Figure 7:
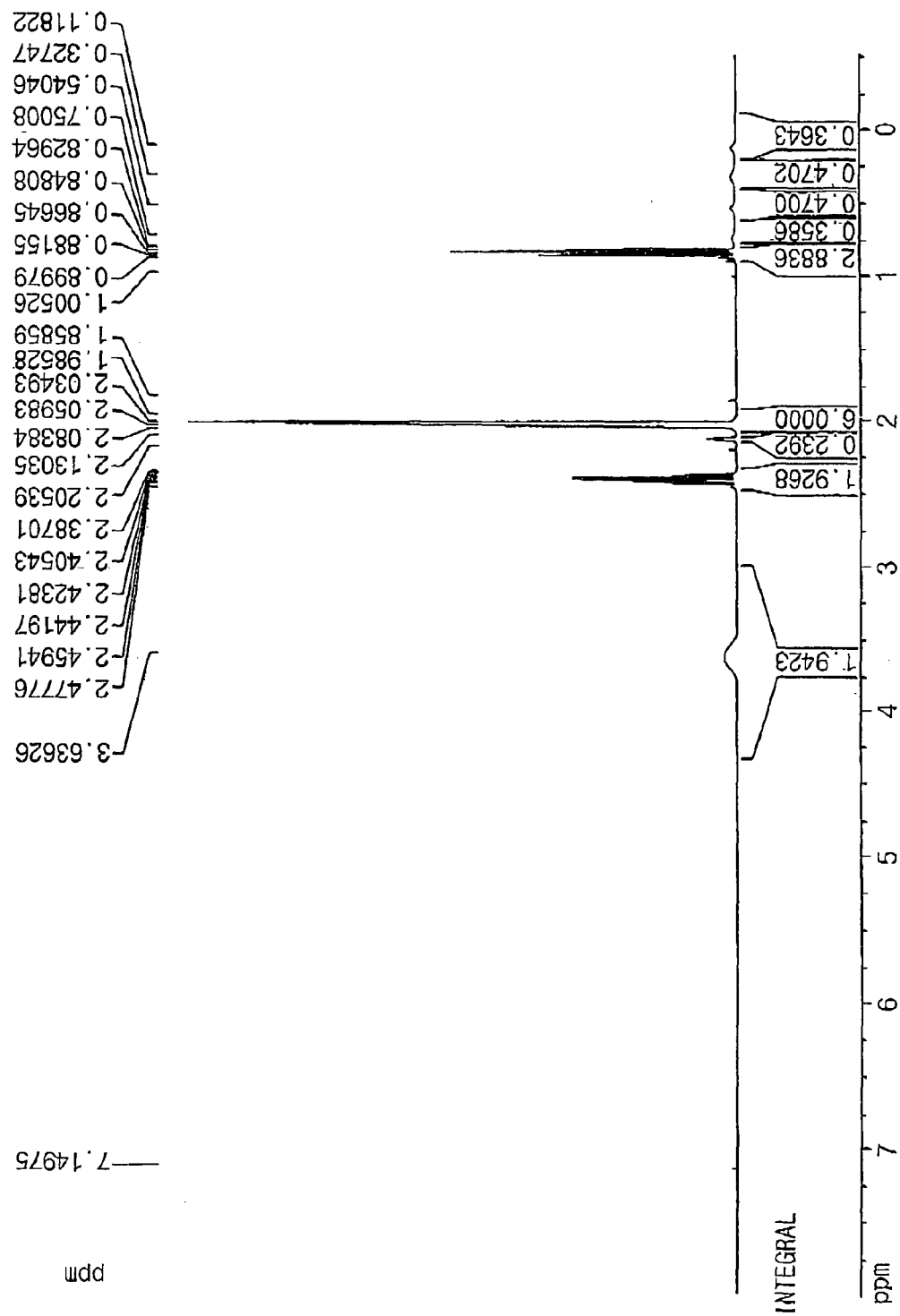

A chemical structure of thus obtained product was analyzed by measuring a hydrogen nuclear magnetic resonance ($^1H$ NMR) spectrum. The $^1H$ NMR spectrum is illustrated in FIG. 7. The obtained product was analyzed as an organometallic compound having a chemical structure represented by Formula 4.

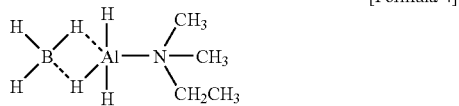

[Formula 4]

COMPARATIVE EXAMPLE 1

Figure 8:
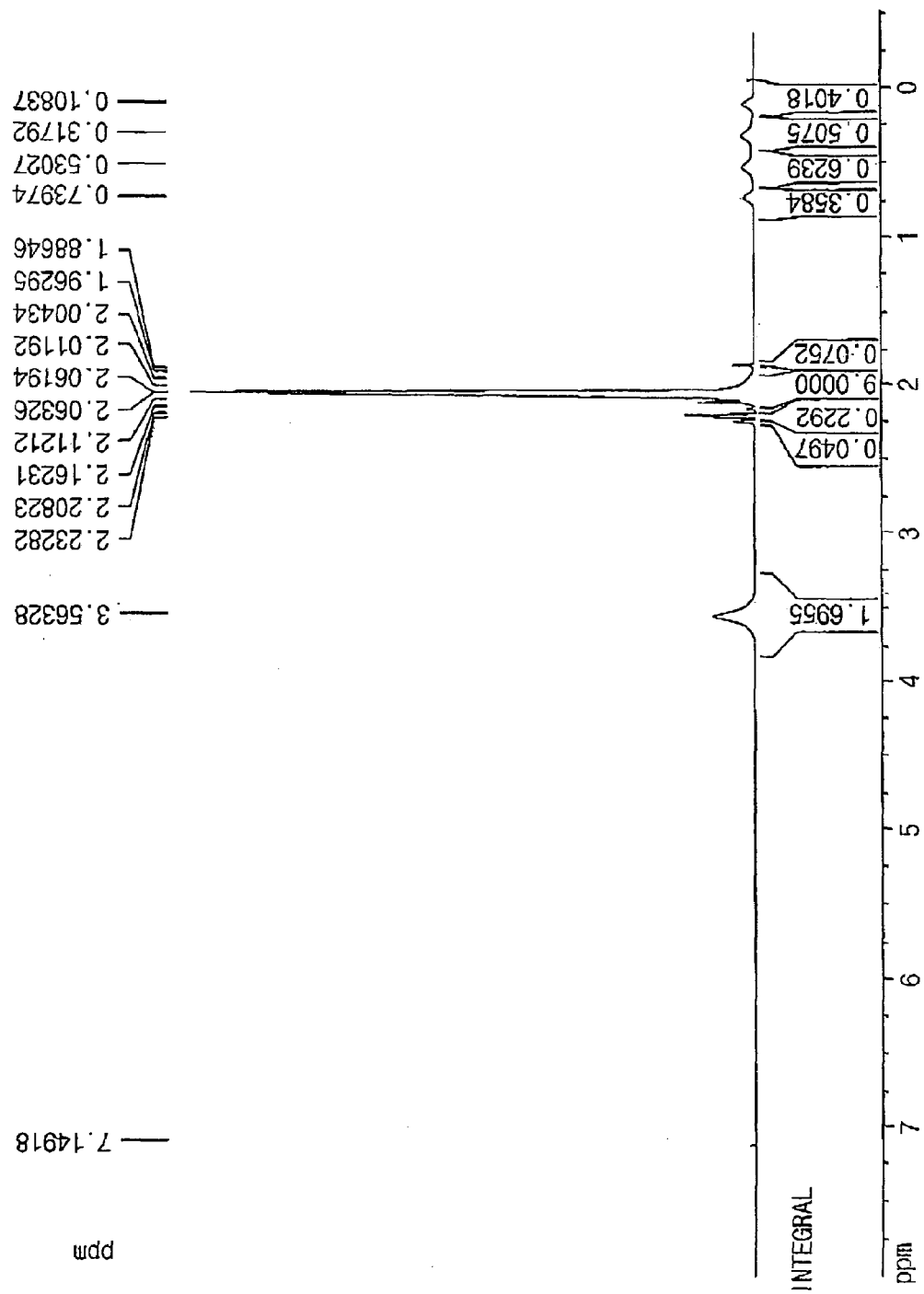

An organometallic compound was prepared by performing a process substantially the same as the process of Example 1, with the exception of using trimethylamine (NMe$_3$) instead of N,N-dimethylethylamine (NEtMe$_2$). A chemical structure of thus obtained product was analyzed by measuring a $^1$H NMR spectrum. The $^1$H NMR spectrum is illustrated in FIG. 8. The obtained product was analyzed as an organometallic compound having a chemical structure represented by Formula 5.

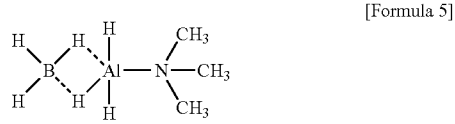

[Formula 5]

Evaluation of polarity of organometallic precursor

Polarities of the organometallic precursors prepared in Example 1 and Comparative Example 1 were evaluated by measuring electrical conductivities of the organometallic precursors. The measured electrical conductivities are shown in Table 1.

TABLE 1

|  | Conductivity [μS/cm] |
| --- | --- |
| Example 1 | 6.0 |
| Comparative Example 1 | 16.6 |

As shown in Table 1, the organometallic precursor prepared in Comparative Example 1, which may include trimethylamine as a ligand, exhibited an electrical conductivity of about 16.6 μS/cm which is higher than about 10 μS/cm, and thus, the organometallic precursor of Comparative Example 1 may have a stronger polarity. However, the organometallic precursor prepared in Example 1, which may include dimethylethylamine as a ligand, showed an electrical conductivity of about 6.0 μS/cm lower than about 10 μS/cm. Thus, the organometallic precursor prepared in Example 1 may have weaker polarity as compared to the organometallic precursor prepared in Comparative Example 1.

Evaluation of Thermal Stability of Organometallic Precursor

Thermal stabilities of the organometallic precursors prepared in Example 1 and Comparative Example 1 were evaluated by measuring variations in a peak height of $^1$H NMR spectrum and a UV-VIS transmittance with the passage of time at temperatures of about 100° C. and about 20° C. The results are illustrated in FIGS. 9 through 12.

Figure 9:
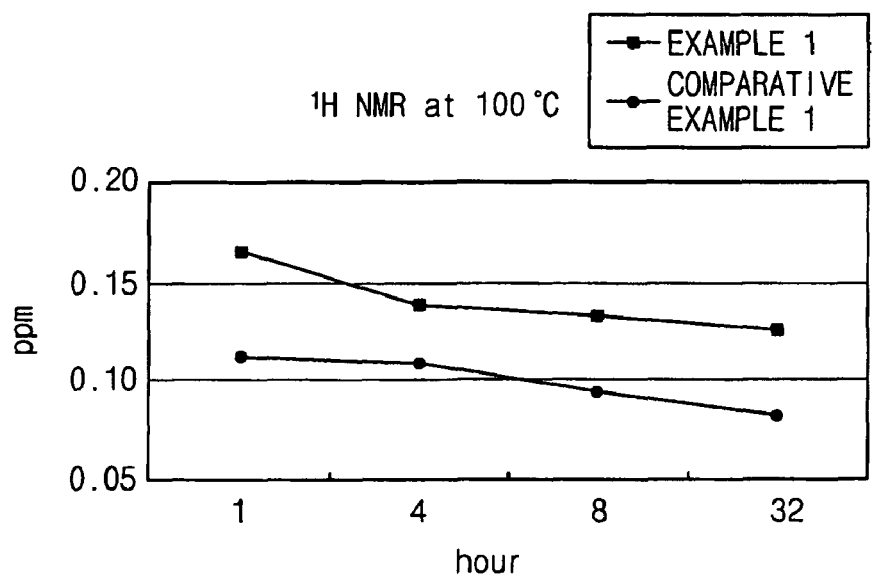
Figure 10:
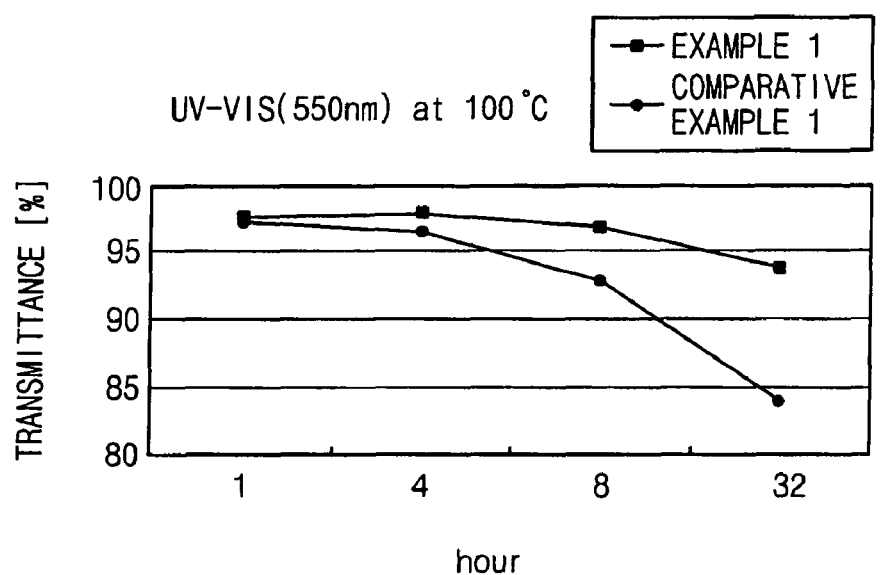
Figure 11:
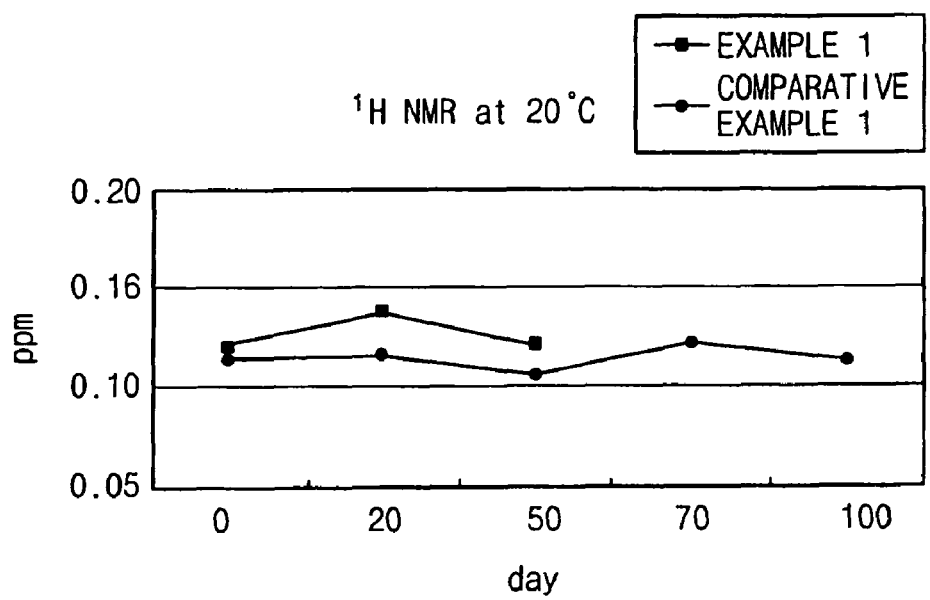
Figure 12:
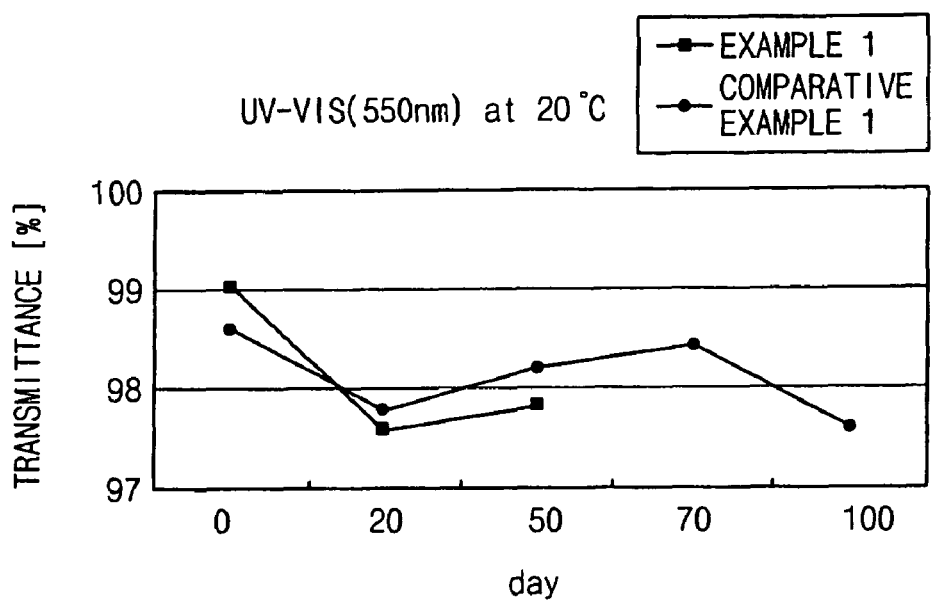

FIGS. 9 and 10 are graphs illustrating variations in a peak height of $^1$H NMR spectrum and a UV-VIS transmittance with the passage of time while the organometallic precursors prepared in Example 1 and Comparative Example 1 were maintained at about 100° C. FIGS. 11 and 12 are graphs illustrating variations in a peak height of $^1$H NMR spectrum and a UV-VIS transmittance with the passage of time while the organometallic precursors prepared in Example 1 and Comparative Example 1 were maintained at about 20° C.

As illustrated in FIGS. 11 and 12, the organometallic precursors prepared in Example 1 and Comparative Example 1 showed similar thermal stabilities at a temperature of about 20° C. However, as illustrated in FIGS. 9 and 10, the organometallic precursor of Comparative Example 1 was abruptly decomposed at a temperature of about 100° C. when about 32 hours passed, whereas the organometallic precursor of Example 1 was not decomposed or was slightly decomposed at a temperature of about 100° C. after about 32 hours passed. Accordingly, the organometallic precursor of Example 1 may have an enhanced thermal stability as compared to the organometallic precursor of Comparative Example 1.

Evaluation of Vapor Pressure and Thermal Analysis of Organometallic Precursor

Physical properties of the organometallic precursors prepared in Example 1 and Comparative Example 1 were evaluated by measuring vapor pressures at several temperatures and by performing a thermal gravimetric analysis (TGA) and a differential thermal analysis (DTA). The results are shown in FIGS. 13 through 15.

Figure 13:
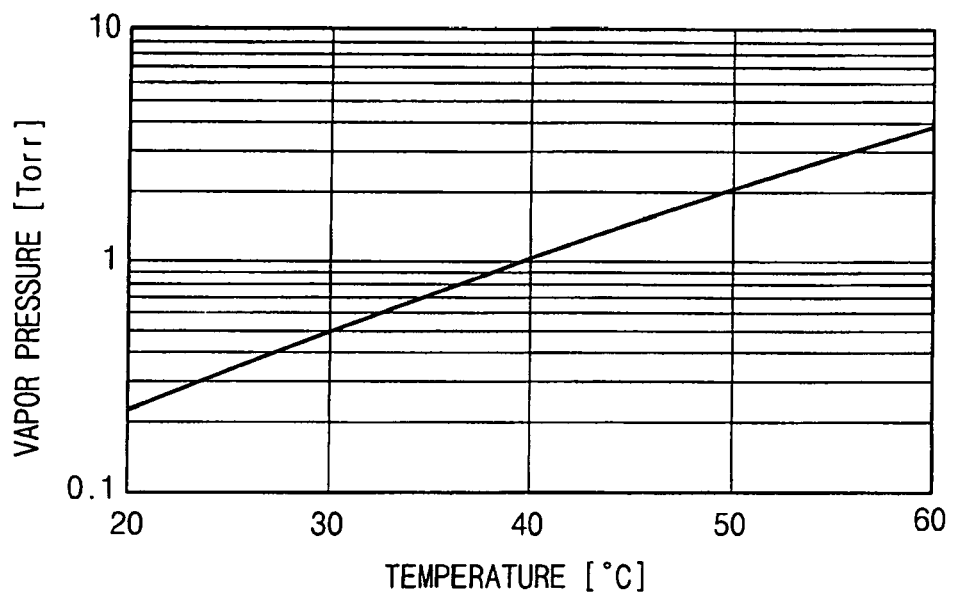

FIG. 13 is a graph illustrating temperature dependency of a vapor pressure of the organometallic precursor prepared in Example 1. FIGS. 14 and 15 are graphs illustrating results of a thermal gravimetric analysis (TGA) and a differential thermal analysis (DTA) with regard to the organometallic precursors prepared in Example 1 and Comparative Example 1.

Referring to FIG. 13, the organometallic precursor prepared in Example 1 exhibited a vapor pressure of about 0.23 Torr at a temperature of about 20° C., a vapor pressure of about 0.5 Torr at about 30° C., a vapor pressure of about 1.2 Torr at about 40° C., and a vapor pressure of about 2.2 Torr at about 50° C. The vapor pressure of the organometallic precursor prepared in Example 1 may have a relatively high vapor pressure at a lower temperature range of about 20° C. to about 50° C., and may be more readily evaporated at the lower temperature range.

Figure 14:
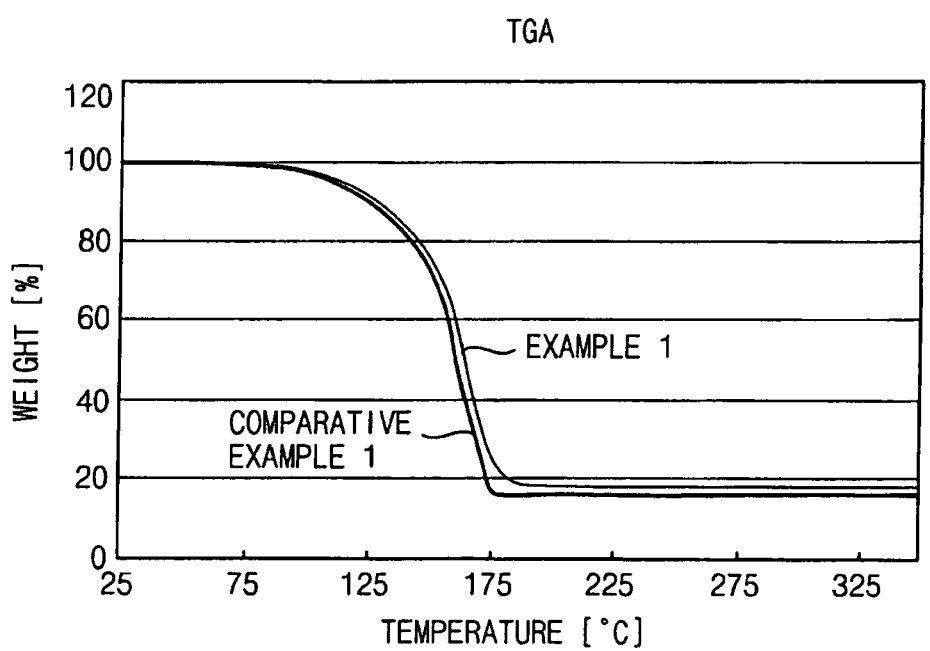
Figure 15:
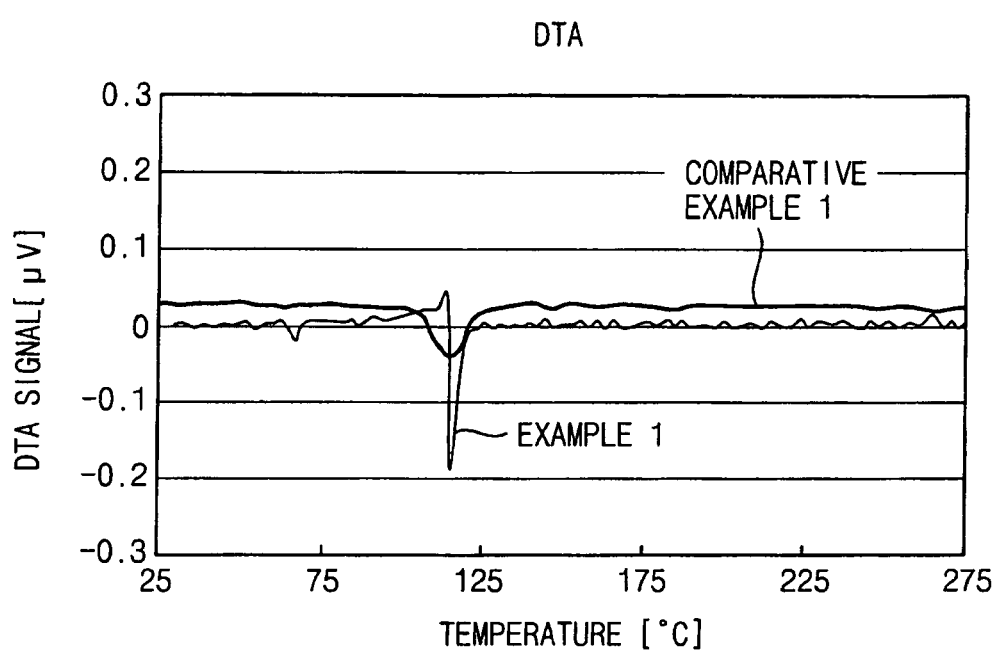

Referring to FIGS. 14 and 15, the organometallic precursor of Example 1 showed a decomposition temperature of about 115° C. Thus, a film may be formed by thermally decomposing the organometallic precursor at a temperature of lower than about 200° C. The decomposition temperature of the organometallic precursor of Comparative Example 1 was similar to the decomposition temperature of the organometallic precursor of Example 1.

Evaluation of Properties of Aluminum Film

Physical properties of aluminum films on wafers in accordance with an increase of the number of the wafers were evaluated by measuring sheet resistance, deposition time and reflective index of the aluminum films, which were formed on the wafers using the organometallic precursors of Example 1 and Comparative Example 1.

The organometallic precursors were vaporized by bubbling with an argon gas in a canister, and aluminum films were formed on several wafers one by one. The aluminum films were formed by a CVD process to have a thickness of about 350 Å. As a process time increased, the number of processed wafers also increased and the amount of the organometallic precursor contained in the canister decreased. Temperatures of several parts in a CVD apparatus are shown in Table 2.

TABLE 2

| | Temperature [° C.] |
|---|---|
| Canister | 25 |
| Hot Can | 27 |
| Gas Line | 30 |
| Shower Head | 35 |
| Chamber | 140 |

Sheet resistance ($R_s$), deposition time and reflective index (RI) of the aluminum films thus obtained were measured.

Figure 16:
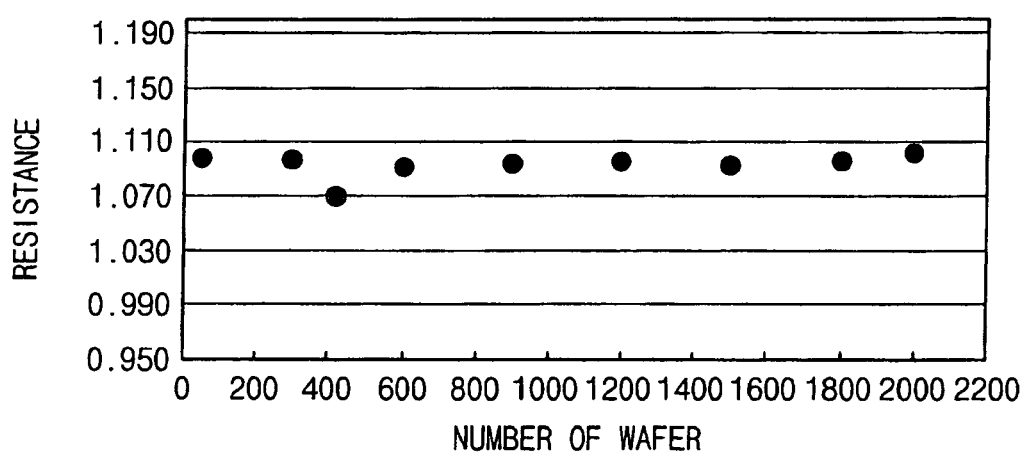

FIG. 16 is a graph illustrating variation of sheet resistances of aluminum films formed on wafers in accordance with an increase of the number of the wafers while the aluminum films were formed using the organometallic precursor of Example 1.

Referring to FIG. 16, the aluminum films formed using the organometallic precursor prepared in Example 1 exhibited sheet resistance constantly maintained even though the number of wafers increased up to about 2,000. The sheet resistance (Rs) may be a value in inverse proportion to a thickness of an aluminum film and a deposition rate. Accordingly, the constant sheet resistance indicates that the thickness of the aluminum films and the deposition rate may also be constantly maintained. This result may be caused by a low polarity and a constant vaporizing rate of the organometallic precursor of Example 1.

Figure 17:
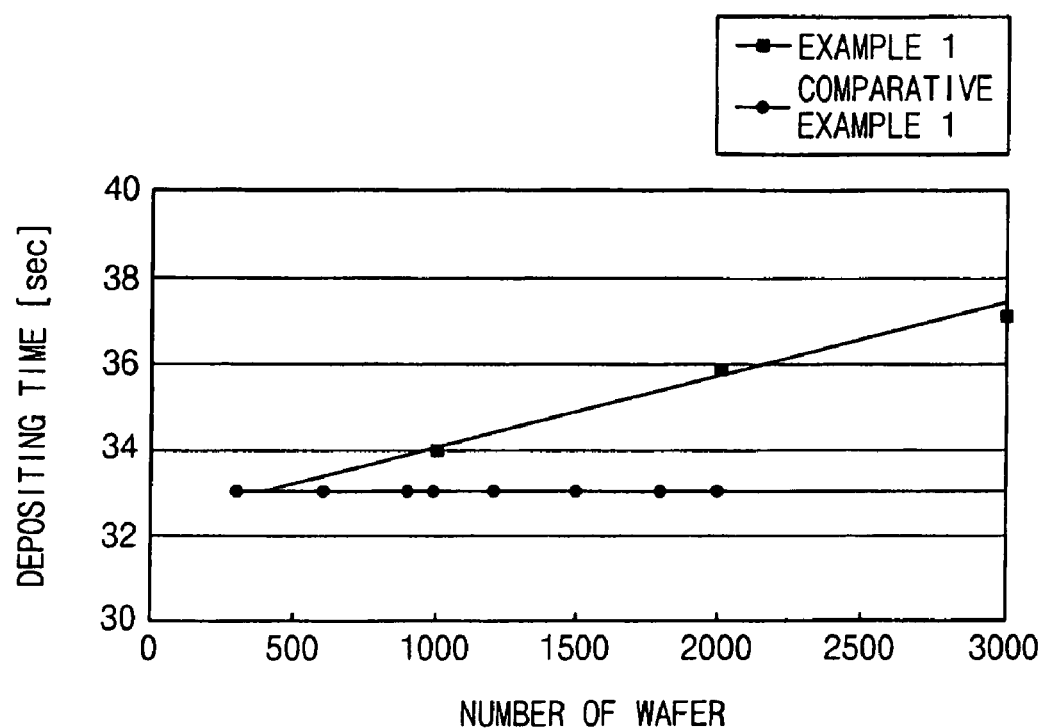

FIG. 17 is a graph illustrating variation of deposition time in accordance with an increase of the number of the wafers while films were formed on the wafers to have a predetermined or given thickness using the organometallic precursor of Example 1 and Comparative Example 1.

Referring to FIG. 17, when the aluminum films were formed on wafers using the organometallic precursor of Comparative Example 1, the deposition time needed for forming a single aluminum film having a predetermined or given thickness increased as the number of wafers increased. Thus, the vaporizing rate and a deposition rate of the organometallic precursor including trimethylamine may decrease in accordance with an increase of the number of processed wafers and a decrease of the amount of precursor in the canister due to higher polarity of the organometallic precursor. However, when the aluminum films were formed using the organometallic precursor of Example 1, the deposition time needed for forming a single aluminum film did not substantially vary while the number of processed wafers reached up to about 2,000. Therefore, the vaporizing rate and a deposition rate of the organometallic precursor including dimethylethylamine may not decrease in accordance with an increase of the number of processed wafers and a decrease of the amount of precursor in the canister due to lower polarity of the organometallic precursor.

Reflective index of the aluminum layers formed using the organometallic precursor prepared in Example 1 was measured. Reflective indexes of an initially formed aluminum layer and an aluminum layer formed about 2,000 times were measured. The results are shown in Table 3.

TABLE 3

| Number of Wafers | Reflective Index (RI) |
|---|---|
| Initial | 225 |
| 2,000 | 227 |

As shown in Table 3, the reflective index of the initial aluminum layer did not substantially vary as compared to the reflective index of the aluminum layer formed about 2,000 times. Reflective index may be a value indicating surface roughness and uniformity of a film. Thus, the organometallic precursor of Example 1 may form metal films (e.g., aluminum films) to have regular surface roughness and uniformity while the metal films were formed on a relatively large number of wafers.

According to example embodiments, the organometallic precursor may include the amine ligand capable of reducing polarity, and thus, interaction between molecules of the organometallic precursor may also be reduced. Due to the reduced molecular interaction, a vaporizing rate of the organometallic precursor may be improved. Further, the vaporizing rate of the organometallic precursor may not be substantially reduced, for example, in a bubbling system while process time passes and/or the amount of the precursor contained in a canister varies. Accordingly, when films are formed on a larger number of wafers using the organometallic precursor, an inflow rate of the precursor and a deposition rate of the film may not be substantially reduced and may be constantly maintained. Thus, films of which thickness and electrical and/or physical characteristics are substantially uniform may be steadily manufactured.

Furthermore, according to example embodiments, the organometallic precursor may have improved thermal and/or chemical stabilities owing to the borohydride ligand. When films are formed using the organometallic precursor, generation of impurities including carbon may be reduced or suppressed to decrease an electrical resistance of the film, and a thermal stress on an underlying structure may be reduced. Therefore, stability, efficiency and/or reliability of a semiconductor manufacturing process may be enhanced.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages of example embodiments. Accordingly, all such modifications are intended to be included within the scope of example embodiments as defined in the claims. In the claims, means-plus-function clauses are intended to cover the structures described herein as performing the recited function and not only structural equivalents but also equivalent structures. Therefore, it may be to be understood that the foregoing may be illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of forming a thin film on a substrate, comprising:
    providing an organometallic precursor onto the substrate, the organometallic precursor including a central metal, a borohydride ligand coordinating to the central metal, and an amine ligand coordinating to the central metal and reducing a polarity of the organometallic precursor; and
    decomposing the organometallic precursor to form the thin film on the substrate,
    wherein the organometallic precursor comprises a compound having a chemical structure represented by Formula 1,

[Formula 1]

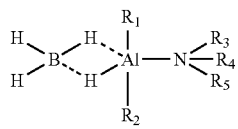

wherein $R_1$ and $R_2$ are each independently $C_1$-$C_4$ alkyl, $R_3$, $R_4$, and $R_5$ are each independently hydrogen, $C_1$-$C_{10}$ alkyl, cycloalkyl or aryl, provided that compounds wherein all of $R_3$, $R_4$, and $R_5$ are hydrogen, methyl, or a combination of hydrogen and methyl are excluded.

2. The method of claim 1, wherein the organometallic precursor is vaporized using a carrier gas in a bubbling system prior to providing the organometallic precursor onto the substrate.

3. The method of claim 1, wherein the organometallic precursor is vaporized at a temperature of about 20° C. to about 50° C. prior to providing the organometallic precursor onto the substrate.

4. The method of claim 1, wherein the organometallic precursor is thermally decomposed at a temperature of about 100° C. to about 300° C.

5. A method of manufacturing a metal wiring, comprising:
    forming an insulation layer on a substrate having a conductive structure;
    partially removing the insulation layer to form an insulation layer pattern having an opening that exposes the conductive structure; and
    forming a first metal film on the insulation layer pattern and a bottom and sidewalls of the opening by using the method of forming the thin film according to claim 1.

6. The method of claim 5, further comprising:
    forming a barrier layer on the insulation layer pattern and a bottom and sidewalls of the opening prior to forming the first metal film.

7. The method of claim 5, wherein the first metal film is formed by a chemical vapor deposition (CVD) process.

8. The method of claim 7, further comprising:
    forming a second metal film on the first metal film by performing a physical vapor deposition (PVD) process.

* * * * *